(12) United States Patent
Collins et al.

(10) Patent No.: US 9,220,581 B2
(45) Date of Patent: Dec. 29, 2015

(54) POROUS IMPLANT DEVICE FOR SUPPORTING A DENTURE

(71) Applicant: Zimmer Dental, Inc., Carlsbad, CA (US)

(72) Inventors: Michael Scott Collins, San Marcos, CA (US); Jeffrey Bassett, Vista, CA (US); Christopher M Gervais, San Marcos, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 1 day.

(21) Appl. No.: 14/199,335

(22) Filed: Mar. 6, 2014

(65) Prior Publication Data

US 2014/0186798 A1    Jul. 3, 2014

Related U.S. Application Data

(63) Continuation of application No. 13/030,283, filed on Feb. 18, 2011, now abandoned.

(51) Int. Cl.
*A61C 8/00* (2006.01)
*A61C 8/02* (2006.01)
(Continued)

(52) U.S. Cl.
CPC .............. *A61C 8/0006* (2013.01); *A61C 8/0012* (2013.01); *A61C 8/0018* (2013.01); *A61C 8/0022* (2013.01); *A61C 8/0048* (2013.01); *A61C 8/0053* (2013.01); *A61L 27/047* (2013.01);
(Continued)

(58) Field of Classification Search
CPC .. A61C 8/0051; A61C 8/0053; A61C 8/0054; A61C 8/0056; A61C 8/0057; A61C 8/0059; A61C 8/0062; A61C 8/0075; A61C 8/0072; A61C 8/0074
USPC ............... 433/172–176, 201.1; 606/301–330; 623/16.11, 17.17, 11.11
See application file for complete search history.

(56) References Cited

U.S. PATENT DOCUMENTS

| 3,797,113 | A | | 3/1974 | Brainin |
| 3,849,887 | A | | 11/1974 | Brainin |
| 4,193,194 | A | * | 3/1980 | Dalise ........................... 433/177 |

(Continued)

FOREIGN PATENT DOCUMENTS

| EP | 2272461 A2 | 1/2011 |
| WO | WO-2012112201 A1 | 8/2012 |

OTHER PUBLICATIONS

"U.S. Appl. No. 13/030,283, Examiner Interview Summary mailed May 6, 2013", 3 pgs.

(Continued)

*Primary Examiner* — Yogesh Patel
(74) *Attorney, Agent, or Firm* — Schwegman Lundberg & Woessner, P.A.

(57) ABSTRACT

A dental implant device has an implant portion for being placed in a bore in bone. The implant portion has a coronal end portion and a porous metal portion. A metal coupling has a coronal end configured for connection to a denture support piece. The coupling also has an apical end integrally formed with the coronal end and engaging the porous metal portion. In one form, the coupling is attached to the porous metal portion in a threaded connection so that the coupling is removable from the porous portion without significantly damaging the porous metal portion sufficiently to re-engage another metal coupling.

10 Claims, 6 Drawing Sheets

(51) Int. Cl.
*A61L 27/04* (2006.01)
*A61C 13/265* (2006.01)

(52) U.S. Cl.
CPC ........... *A61C 8/0068* (2013.01); *A61C 13/2656* (2013.01)

(56) References Cited

U.S. PATENT DOCUMENTS

| | | | |
|---|---|---|---|
| 4,431,416 A | 2/1984 | Niznick | |
| 4,439,152 A | 3/1984 | Small | |
| 4,540,367 A * | 9/1985 | Sulc | 433/181 |
| 4,547,327 A | 10/1985 | Bruins et al. | |
| 4,826,434 A | 5/1989 | Krueger et al. | |
| 5,049,074 A | 9/1991 | Otani et al. | |
| 5,195,891 A | 3/1993 | Sulc | |
| 5,254,005 A | 10/1993 | Zuest | |
| 5,310,343 A | 5/1994 | Hasegawa et al. | |
| 5,417,570 A | 5/1995 | Zuest et al. | |
| 5,520,540 A * | 5/1996 | Nardi et al. | 433/172 |
| 5,607,607 A | 3/1997 | Naiman et al. | |
| 5,704,788 A | 1/1998 | Milne | |
| 5,934,287 A | 8/1999 | Hyashi et al. | |
| 6,030,219 A | 2/2000 | Zuest et al. | |
| 6,095,817 A | 8/2000 | Wagner et al. | |
| 6,217,331 B1 | 4/2001 | Rogers et al. | |
| 6,227,859 B1 | 5/2001 | Sutter | |
| 6,299,447 B1 * | 10/2001 | Zuest et al. | 433/172 |
| 6,419,491 B1 | 7/2002 | Ricci et al. | |
| 6,454,569 B1 | 9/2002 | Hollander et al. | |
| 6,695,616 B2 | 2/2004 | Ellison | |
| 7,021,934 B2 | 4/2006 | Aravena | |
| 7,959,439 B2 * | 6/2011 | Bulloch et al. | 433/173 |
| 8,043,089 B2 * | 10/2011 | Bulard et al. | 433/173 |
| 2008/0050699 A1 | 2/2008 | Zhang et al. | |
| 2009/0023109 A1 | 1/2009 | Jinton et al. | |
| 2009/0036908 A1 | 2/2009 | Zokol et al. | |
| 2010/0003639 A1 | 1/2010 | Salvi et al. | |
| 2010/0003640 A1 * | 1/2010 | Damstra et al. | 433/201.1 |
| 2010/0055645 A1 | 3/2010 | Mullaly et al. | |
| 2010/0114314 A1 | 5/2010 | Lomicka et al. | |
| 2010/0145393 A1 | 6/2010 | Fallin et al. | |
| 2010/0184004 A1 * | 7/2010 | Fromovich | 433/174 |
| 2012/0214128 A1 | 8/2012 | Collins et al. | |

OTHER PUBLICATIONS

"U.S. Appl. No. 13/030,283, Examiner Interview Summary mailed Sep. 24, 2012", 3 pgs.

"U.S. Appl. No. 13/030,283, Final Office Action mailed Jan. 9, 2013", 11 pgs.

"U.S. Appl. No. 13/030,283, Non Final Office Action mailed May 25, 2012", 11 pgs.

"U.S. Appl. No. 13/030,283, Non Final Office Action mailed Nov. 7, 2013", 9 pgs.

"U.S. Appl. No. 13/030,283, Response filed May 14, 2013 to Final Office Action mailed Jan. 9, 2013", 12 pgs.

"U.S. Appl. No. 13/030,283, Response filed Sep. 25, 2012 to Non Final Office Action mailed May 25, 2012", 16 pgs.

"U.S. Appl. No. 13/030,283, Restriction Requirement mailed Apr. 4, 2012", 6 pgs.

"International Application Serial No. PCT/US2011/060414, International Preliminary Report on Patentability mailed Aug. 29, 2013", 10 pgs.

"International Application Serial No. PCT/US2011/060414, International Search Report mailed Feb. 2, 2012", 5 pgs.

"International Application Serial No. PCT/US2011/060414, Response filed Mar. 2, 2012 to International Search Report and Written Opinion mailed Feb. 2, 2012", 9 pgs.

"International Application Serial No. PCT/US2011/060414, Written Opinion mailed Feb. 2, 2012", 9 pgs.

* cited by examiner

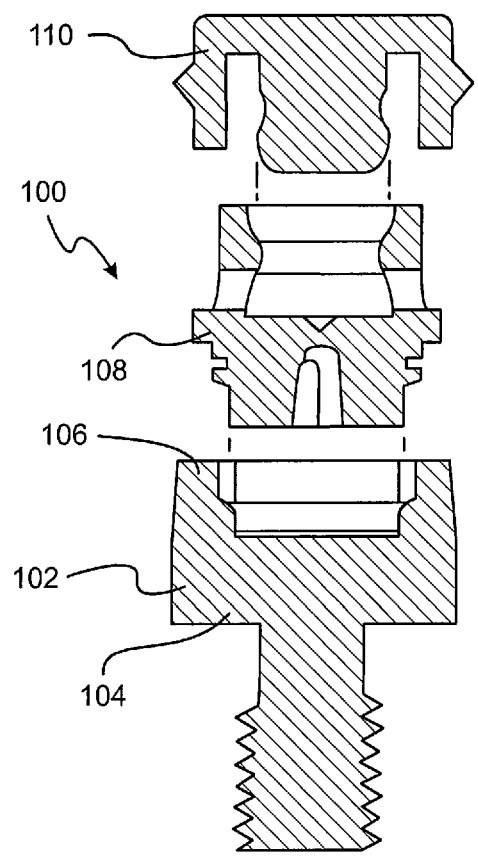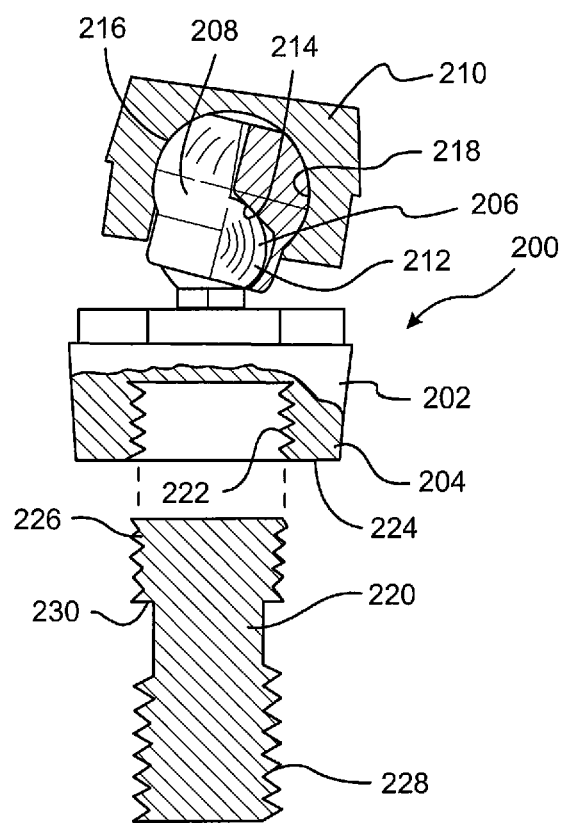
FIG. 3
FIG. 4

POROUS IMPLANT DEVICE FOR SUPPORTING A DENTURE

CLAIM OF PRIORITY

This application is a continuation of U.S. patent application Ser. No. 13/030,283, filed on Feb. 18, 2011, the benefit of priority of which is claimed hereby, and which is incorporated by reference herein in its entirety.

BACKGROUND OF THE INVENTION

1. Field of the Invention

The present invention relates to porous implants and, in particular, to a porous dental implant with improved osseointegration features and that anchor dentures.

2. Description of the Related Art

Conventional dentures have prosthetic teeth shaped and colored to appear like natural teeth. The base of the denture is colored to match gingival or soft tissue, and is fixed upon a patient's gingiva by an adhesive. Oftentimes, however, the denture does not adhere well to the patent's gum causing significant discomfort and malfunction of the denture as well as embarrassment to the patient when the denture slips out of the patient's mouth.

In this case, endosseous implants may be used to anchor the denture to support multiple prosthetic teeth. A denture that fits over implants, or shortened natural teeth if preserved, is called an overdenture.

Endosseous dental implants are typically threaded or press-fit into pre-drilled bores in the mandible or maxilla to support one or more prosthetic teeth. A number of implants spaced along the mandible or maxillae may be used to support a full or partial overdenture. The overdenture is used when the mandible or maxilla of a patient has insufficient bone mass or strength to hold an implant for each tooth, or when such a surgery for so many implants is cost prohibitive or otherwise harmful to the patient. A full denture with prosthetic teeth for an entire upper or lower jaw is usually anchored by two to four implants. The denture may be permanently fixed to the implants or may be removable in a snap-fit arrangement. More stable systems have bars interconnecting adjacent implants and that are covered by an overdenture snapped onto the bars.

However, many years of denture use often result in a reduced alveolar ridge or bone resorption caused by reduced impact from occlusal forces. The localized impact of occlusal forces on the mandible or maxilla is reduced because the denture causes the forces to be impacted by the soft tissue throughout the mandible or maxilla. In this case, further support systems may be needed to hold the denture in a stable position. However, installing even a reduced number of implants for supporting a denture may be too expensive because the alveolar ridge may need to be built up by grafts for example to adequately support a full size implant. Also, grafting procedures often require harvesting bone from other parts of the body or using animal or cadaver bone. The grafting procedure can be painful, the grafts may fail to integrate, and the procedure has some risks such as infection or disease transmission if animal or cadaver bone is used. In other high risk cases such as smokers, diabetics, or osteoporotics that have substantially reduced or missing bone mass, low bone density, and/or abnormally slow bone growth, obtaining adequate support for conventional, full size dental implants may be impossible. Thus, a desire exists to increase the strength of the osseointegration, increase the rate of growth of the osseointegration, and reduce the required size of the dental implant.

BRIEF DESCRIPTION OF THE DRAWINGS

FIG. 3 is a side, cross-sectional, and exploded view of a second denture support system;

FIG. 4 is a side, cross-sectional, and partially exploded view of a third denture support system;

DETAILED DESCRIPTION

Figure 1:
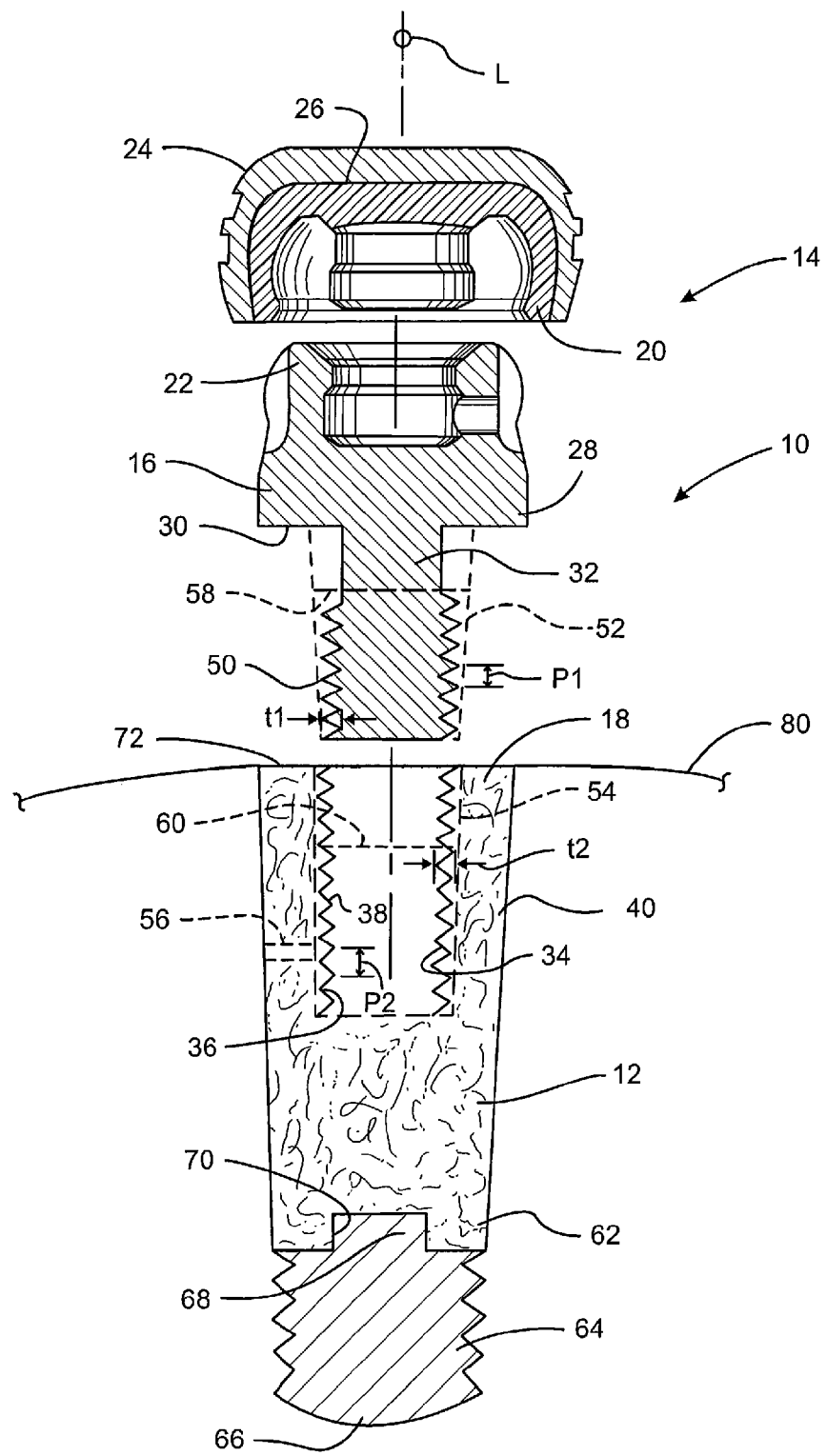
FIG. 1 is a side, cross-sectional and exploded view of an implant device with a first denture support system.

Referring to FIG. 1, an implant device 10 has an implant or implant portion 12 that supports a denture support system 14. Herein, denture refers to a dental prosthetic appliance that distributes occlusal forces along the mandible or maxillae, and through the gingiva or gums, rather than having a single tooth shaped prosthesis supported by a single implant to directly impact occlusal forces. A denture, and specifically an overdenture, also may distribute the occlusal forces among one or more implants supporting the denture. The denture may have one or more prosthetic teeth supported by a gum colored base, usually made of a polymer that is placed over the top and sides of the gums to distribute the occlusal forces thereon. The denture may also be adhered to the gums. This denture may be a full or complete denture that covers an entire mandible or maxillae or may be a shortened partial denture that only supports one or more prosthetic teeth. In the illustrated form, the denture is supported by both soft tissue and one or more implants.

Denture support system 14 includes a base or coupling 16 (also referred to as an abutment portion) that connects to a coronal end portion 18 of the implant 12, a locator element 20 that snap-fits onto a coronal end portion 22 of the coupling 16, and a cap 24 that snap-fits onto a coronal end portion 26 of the locator element 20.

With such a system, a denture or appliance has one or more recesses arranged along an arc on the underside of the appliance to align with a patient's mandible or maxillae. Each recess receives a cap 24. In the patient's mouth, implants 12 are press-fit or threaded into bores spaced along the mandible or maxillae 80. A coupling 16 is then mounted on each implant 12. Then, to mount the appliance on the jaw (jaw herein refers to either the maxillae or mandible), each locator element 20 is either snap-fit onto a coupling 16 or into the cap 24. The appliance is then snap-fit onto the couplings 16 in the patient's mouth by pressing the locator elements 20 onto the other piece (coupling 16 or cap 24) it snap-fits onto. The locator element 20 is typically made of a resilient material for this purpose such as an elastic polymer. This type of system provides an easily removed appliance that is more secure than dentures solely adhered to the top and sides of the gums, and lower cost than a more permanent system that has bars to support the denture or appliance. As explained in greater detail below, a number of different denture support systems may be used with implant 12.

Figure 2:
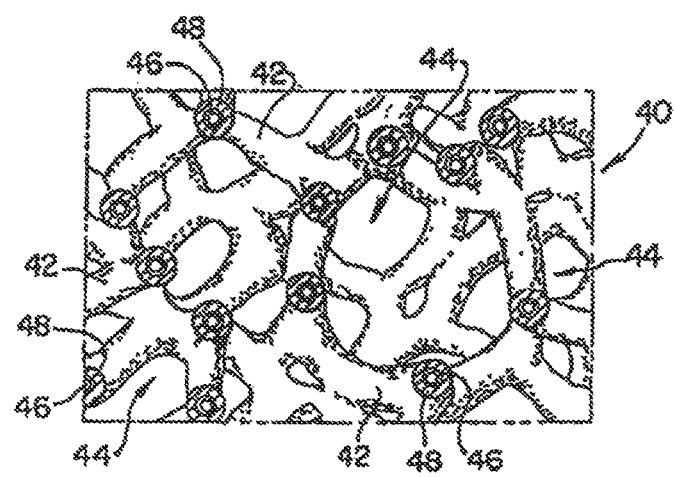
FIG. 2 is a close-up, fragmentary view of a porous material on the implant device of FIG. 1.

Referring to FIGS. 1-2, to improve osseointegration, the implant 12 includes a porous metal portion 40, and specifically, a porous tantalum portion which is a highly porous biomaterial useful as a bone substitute and/or cell and tissue receptive material. An example of such a material is produced using TRABECULAR METAL™ technology generally available from Zimmer, Inc. of Warsaw, Ind. TRABECULAR METAL™ is a trademark of Zimmer Technology, Inc. Such material may be formed from a reticulated vitreous carbon foam substrate which is infiltrated and coated with a biocompatible metal, such as tantalum, etc., by a chemical vapor deposition ("CVD") process in a manner disclosed in detail in U.S. Pat. No. 5,282,861, the disclosure of which is fully incorporated herein by reference. Other metals such as niobium, or alloys of tantalum and niobium with one another or with other metals may also be used.

As shown in FIG. 2, porous tantalum structure 40 includes a large plurality of members 42 (also called ligaments, branches, or struts) defining open spaces 44 therebetween, with each member 42 generally including a carbon core 46 covered by a thin film of metal 48 such as tantalum, for example. The open spaces 44 between members 42 form a matrix of continuous channels having no dead ends, such that growth of cancellous bone entirely through porous tantalum structure 40 is uninhibited. The porous tantalum may include up to 75%-85% or more voids therein. Thus, porous tantalum is a lightweight, strong porous structure which is substantially uniform and consistent in composition, and closely resembles the structure of natural cancellous bone, thereby providing a matrix into which cancellous bone may grow to anchor implant 12 into the surrounding bone of a patient's jaw which increases stability. The rough exterior surface of such porous metal part has a relatively high friction coefficient with adjacent bone forming the bore that receives the implant to further increase initial stability as alluded to above. This structure can produce superior aesthetic results by restricting movement of the implant. These implants can be placed without supplementary surgical procedures, such as bone grafting, and can be placed in areas where traditional implants have been less successful, such as with reduced or decayed alveolar sections.

More specifically, the high level of friction between the porous material and the bone provides immediate stability post surgery. The tantalum members or struts 42 that extend from the surface of the material create a rasping action that may stimulate bone growth and anchor the implant at the time of placement. The extremely biocompatible tantalum metal that the porous material is made from allows bone to directly oppose the material. The tantalum forms a porous scaffolding that allows bone to grow into the material providing a rapid osseointegration response that quickly augments the initial mechanical fixation to secure the implant. The implant with in-grown bone may have stability greater than a comparably sized implant with only on-grown bone. Finally, the composite of in-grown bone and such a porous material has elastic properties much closer to bone than a solid metal implant, creating a loading environment that is conducive to maintaining bone near the implant.

Regarding the initial stability, as an implant with the porous material is inserted into the bore or cavity in bone, the porous material will bite into the bone by grating, chipping and/or flaking bone pieces off of the bone sidewalls against which the implant device is being placed. When the implant is placed into the bore or cavity, this "rasping" action may form slight recesses or indents within the sidewall. This restricts rotational or twisting motion of the implant device within the bore or cavity when the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. Thus, the porous material has increased resistance to twisting or rotation, allows for immediate or very early loading, and increases long-term stability due to the improved osseointegration. Such an implant with ingrown bone has stability greater than a comparably sized implant with only on-grown bone. These advantages may be realized no matter the form of the porous implant (e.g., root-form or a larger implant block as described in detail below).

Porous tantalum structure 40 may be made in a variety of densities in order to selectively tailor the structure for particular applications. In particular, the porous tantalum may be fabricated to virtually any desired porosity and pore size, whether uniform or varying, and can thus be matched with the surrounding natural bone in order to provide an improved matrix for bone in-growth and mineralization. This includes a gradation of pore size on a single implant such that pores are larger on an apical end to match cancellous bone, and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all, or some of the pores with a solid filler material.

To provide additional initial mechanical strength and stability to the porous structure, the porous structure may be infiltrated with a filler material such as a non-resorbable polymer or a resorbable polymer. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include polylactic co-glycolic acid (PLGA), polylactic acid (PLA), polyglycolic acid (PGA), polyhydroxybutyrate (PHB), and polyhydroxyvalerate (PHV), and copolymers thereof, polycaprolactone, polyanhydrides, and polyorthoesters. By providing additional initial mechanical strength and stability with a resorbable filler material, a titanium reinforcing implant core may not be required when directly impacting mastication forces from a single prosthetic tooth. The resorbable material would resorb as the bone grows in and replaces it, which maintains the strength and stability of the implant.

This strong porous structure is particularly beneficial when reduced alveolar ridges are present. In this case, the implant 12 may be less than about 4 mm in total height (along the apical-coronal direction), and in one form is about 2.3 to 3.3 mm in total height. Otherwise, the implant may have typical sizes such as up to about 16 mm in total height.

Referring again to FIG. 1, the coupling 16 has an apical end portion 28 that engages the implant 12. In one form, the apical end portion 28 is integrally formed with the coronal end portion 22 of the coupling 16, but could be separate. The coupling 16 as well as the cap 24 may be made of a biocompatible metal such as titanium, titanium alloy, stainless steel, zirconium, cobalt-chromium molybdenum alloy, polymers such as polyether ketone ketone (PEKK) for one example, ceramic, and/or composite material.

The apical end portion 28 may be configured for temporary or permanent attachment to the porous metal portion 40 of the implant 12. In the illustrated form, the apical end portion 28 has an apical engagement surface 30 and a shaft or extension 32 extending apically from the engagement surface 30. The porous metal portion 40 has an axially extending bore 34 to receive the shaft 32. A wall 36 defines the bore 34 with pre-formed internal threads 38 to engage exterior threads 50 on the shaft 32. To form the threads 38, a steel coil is rotated into the bore 34 to cut into the porous wall 36 to form the threads 38 thereon. Alternatively, the thread 38 may be formed by a pre-tapped or machined insert typically made of Ti, or by electro discharge machining. In one example form, the maximum diameter of the bore 34 is about 1 to 2 mm to the base of the threads 38, and the threads 38 may be sized as type 1-72 with a pitch of about 0.014 inches. The pitch is measured as the axial or longitudinal length between adjacent single lead thread peaks. The threads 38 may alternatively be triple lead threads with a pitch of 0.042 inches. The axial length of the threads is at least about 1 mm although the threads may have other lengths as desired to withstand pull-out of the coupling 16.

It may be desirable to form a connection in the bore 34 that permits the coupling 16 to be removed from the implant 12 and replaced when the coupling 16 or support system 14 is damaged or the type of denture support system is to be changed. Thus, damage to the porous thread 38 should be prevented or limited when the coupling 16 is removed from the bore 34 so that the implant 12 can adequately support a denture with a replacement coupling that may be metal, ceramic, or other material for long term placement and not merely a coupling considered to be temporary, such as a temporary polymer coupling for example. To limit such damage to the thread 38, the thread is formed with relatively loose fitting threads such as class 1 thread specifications under the ASME B.1.1. standard. The measurement for the tightness or looseness of the threaded connection is indicated by the pitch allowance, which is the difference between the maximum pitch (or pitch length) of the external threads and the minimum pitch of the internal threads with respect to the pitch length tolerances.

Smaller diameters of class 1 threads are not defined as standard threads in the thread specifications, but allowances for a looser configuration of the thread can be calculated. When the implant manufacturer designs and fabricates both the male and female threads, an acceptable fit for the application can be assured. For a 1-72, class 1 thread, the maximum pitch P1 (FIG. 1) on the external threads 50 of the coupling 16 is no greater than about 0.0143311 inches while the minimum internal thread pitch P2 (FIG. 1) on the implant 12 is no less than about 0.013467 inches, for a maximum desired pitch allowance of about 0.000844 inches. In another form, the minimum pitch allowance is at least about 0.0008 inches.

In order to further reduce the risk of damaging the internal threads 38, the thread depth t2 (FIG. 1) of the internal threads 38 on the implant 12 is at most about 70% of the thread depth t1 (FIG. 1) of the external threads 50 on the coupling 16. In one form, the coupling thread depth t1 is about 0.0075 inches and the implant thread depth is at most about 0.00525 inches. This structure reduces the amount of surface area on the threads 38 of the implant that is susceptible to damage without significantly reducing the strength of the threaded connection.

Typically, a stand-alone, single-tooth implant that receives a full occlusive force, such as about 68 lb/sq. in (about 300 N) cannot have a connection with such a wide tolerance because these types of connections often do not withstand such relatively large occlusive forces over long time periods. Here, however, for a complete denture, four implants 12 will typically be used to support four snap-fit locations, although less or more may be used as desired. Thus, in this case, a single implant on such a denture system should not receive the full occlusive force. At least some of the force may be absorbed by the soft tissue, and in turn along the jaw, and the remainder of the force may be spread at least partially among the implants. The implants on the system, together, may only be impacted by about 75%, 50%, or even 20% of the total occlusive force. Even if the implants are found to impact 100% of the occlusive force rather than partially impacted on the soft tissue and the jaw, the force is spread among the implants of the system so that a single implant substantially does not receive 100% of the force.

Alternatively, a more permanent connection can be provided between the coupling 16 and the porous metal portion 40 of the implant 12. This may include self-tapping threads on the shaft 32 that cuts into the porous wall 34 of the implant to form a permanent threaded connection. Otherwise, a friction fit may be used between a non-threaded shaft 52 (shown in dash line on FIG. 1) that is generally cylindrical and may have an axially extending morse taper as shown. The shaft 52 is press-fit into a bore 54 (also shown in dash line) on the implant 12. In this case, the outer diameter of the shaft 52 is about $10/1000$ inches wider than the inner diameter of bore 54.

As another alternative, a shrink fit may be used with a Ti shaft that will shrink upon exposure to liquid nitrogen, for example, and is then cooled to expand within bore 54 resulting in a tight fit within the bore 54. Also, the shaft 32 or 52 may be respectively locked into the bore 34 or 54 by a separate member such as a cross-pin or set screw 56 (shown in dashed line). Such a pin or screw may or may not pass entirely through the coupling shaft and to the porous material on the other side of the shaft. Otherwise, the apical end portion 28 may be connected to the porous metal portion 40 by a diffusion bond or a chemical vapor deposition bond. In this case, the coupling 16 may have a relatively short, central locating shaft 58 (shown in dashed line on FIG. 1) received by a short bore 60 (also shown in dashed line) on the implant 12 for centering the coupling 16 on the implant 12. The bonding takes place between the shaft 58 and the bore 60, or between the engagement surface 30 and the coronal end portion 18, or both.

An apical end portion 62 of the porous metal portion 40 may be similarly bonded to a non-porous anchor or stem 64 forming an apical end 66 of the implant 12. In one form, the anchor 64 is made of titanium, titanium alloy, stainless steel, zirconium, cobalt-chromium molybdenum alloy, polymers such as polyether ketone ketone (PEKK) for one example, ceramic, and/or composite material. The anchor 64 also has external threads for strong connection to cancellous bone and may be self-tapping threads for screwing the implant 12 into a bore in bone. As with the bonded connection to the coupling 16, the anchor 64 may also have a short locating shaft 68 received in a central bore 70 on the apical end portion 62.

When a more permanent connection is used, implant 12 is effectively a one-piece implant that extends through the gingiva once implanted. Whether the connection between the coupling 16 and implant 12 is a more temporary connection or a permanent connection, the implants 12 can be fully loaded with the denture immediately after surgery since the occlusal loads are reduced as explained above. In other cases, where appliances apply a more direct load on the implant, an overdenture that is not tightly secured to the implants may be used during a healing period.

As mentioned above, the coupling 16 may be disconnected from implant 12 without significantly damaging the porous metal portion 40. The coupling 16 may be removed to replace it if it is damaged. Also, other interchangeable couplings may be provided, each for a different denture support system. Each of the couplings has an apical end the same or similar to the apical end 28 on the coupling 16 for connection to the implant 12 so that the type of support system on the implant 12 may be changed.

For example, support system 14 (FIG. 1) is similar to the LOCATOR® support system provided by Zest Anchors, Inc. Coupling 16 may be removed from implant 12 to replace it with a support system 100 (FIG. 3) or a support system 200 (FIG. 4). In the illustrated example, support system 100 may be similar to the ERA® system provided by Sterngold, Inc. Support system 100 includes a coupling 102 with an apical end portion 104 for connection to the implant 12 and a coronal end portion 106 for connection to a female element 108 in a snap-fit. A male, resilient cap 110 is mounted on the female element 108. The cap 110 may be placed directly in a recess in a denture as explained above for cap 24.

Referring to FIG. 4, an alternative denture support system 200 also may be mounted on the implant 12. The support system 200 has a coupling 202 with an apical end portion 204 for engagement with the implant 12 and a coronal end portion 206 configured for connection to a connector element 208. A cap or female element 210 is mounted on the connector element 208 and fits within a recess on a denture. Instead of the couplings 16 and 102 described above with a recess opening coronally for receiving a projection of the denture support piece, the coupling 202 has a male connector, and in one specific example, a ball 212 that fits within a socket 214 formed on the connector element 208. In turn, the connector element 208 has a spherical outer surface 216 that fits within a socket 218 in the cap 210 to form a second ball joint.

Also with support system 200, a separate shaft 220 is received in a bore 222 open on an apical surface 224 of the coupling 202, thereby forming a female connector on the coupling rather than an integral male connector as with couplings 16 and 102. The shaft 220 may be threaded on both its coronal end 226 and its apical end 228 to connect the coupling 202 to the implant 12. In the illustrated form, the coronal end 226 may have a larger outer diameter than its apical end 228 to form a shoulder 230 therebetween. The shoulder 230 sits on a coronal surface 72 of the porous metal portion 40 of the implant 12 (FIG. 1) so that advancement of the shaft 220 into the bore 34 is limited to ensure a sufficient amount of the coronal end 226 extends above the implant 12 for connection to the bore 222 and the coupling 202. It will be understood that any of the support systems described herein may be provided with such a separate shaft rather than the integral shaft as provided with couplings 16 and 102.

Figure 5:
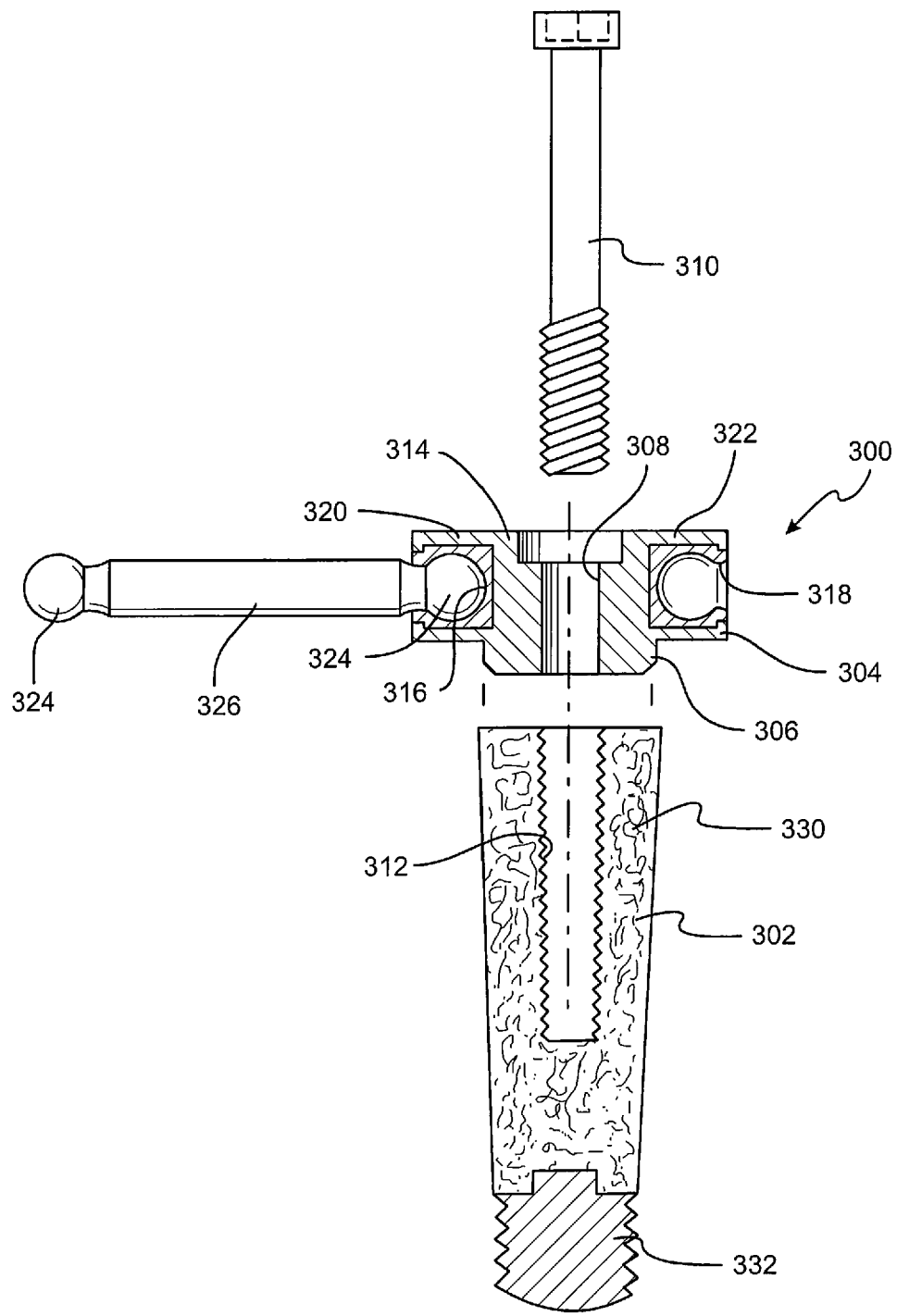
FIG. 5 is a side, cross-sectional, and partially exploded view of an implant with a fourth denture support system.

Referring to FIG. 5, the coupling 16 may also be removed to replace the temporary support systems 14, 104, or 204 with a more permanent bar support system. This system provides bars or beams that extend from implant to implant spaced along an arch on the mandible or maxilla. A denture then snaps on and off of the bars. The bars, however, remain extending horizontally and coronally of the soft tissue. Although such a permanent system is more costly, it may reduce slight shifting of the denture in the mouth to provide a more stable and comfortable feeling because the denture can attach to the fixed bars in a relatively large number of locations.

In the illustrated form, a denture support system 300 has an implant 302, similar to implant 12, including a stem 332 like stem 64. The system 300 also has a coupling 304 mounted on the implant 302. The coupling 304 has an apical end portion 306 configured to engage a porous metal portion 330 of the implant 302 and has an axially extending through-bore 308. A fastener 310 extends through the through-bore 308 and into an internal bore 312 on the implant 302 to retain the coupling 304 on the implant 302. The internal bore 312 may be longer than the bore 32 on implant 12 to alternatively receive both the longer fastener 310 as well as the couplings 16, 102, or 202 for example. For this purpose, the internal bore 312 may also have an axial section with a larger diameter (a more coronal section for example) and an axial section with a smaller diameter (such as a more apical section) to accommodate different diameters on both the fastener 310 and the shaft 32 and 220 from the other couplings.

The coupling 304 also has a coronal portion 314 with one or two recesses 316 and 318 that opens in a mesial or distal direction (or laterally relative to the coronal-apical direction). In the illustrated form, each recess 316 and 318 is placed on a horizontal extension 320 or 322 respectively. Each of the recesses 316 and 318 receives an end 324 of a horizontally extending bar 326 that spans from coupling to coupling 304 mounted on the implants 302 along the mandible or maxillae. The overdenture has underlying structures that snap onto each bar on one or more places and covers the bar and the coupling.

In addition to these examples, any denture support system on the implants herein may have any connection between the coupling and the other support system pieces as long as the denture is adequately supported, and the implant receives sufficiently reduced occlusive forces if the coupling is directly attached to the porous material by a threaded connection.

It will be understood that it is also possible to replace the coupling 16 to have the implant support an abutment and a single prosthetic tooth instead of the denture. The latter case, however, would only be recommended in cases where the new coupling can be permanently bonded to the implant, or the implant internal bore can be modified to connect to the coupling in a configuration sufficient to impact single-tooth occlusive forces without damaging or displacing the implant in the mandible or maxilla.

Figures 6, 7:
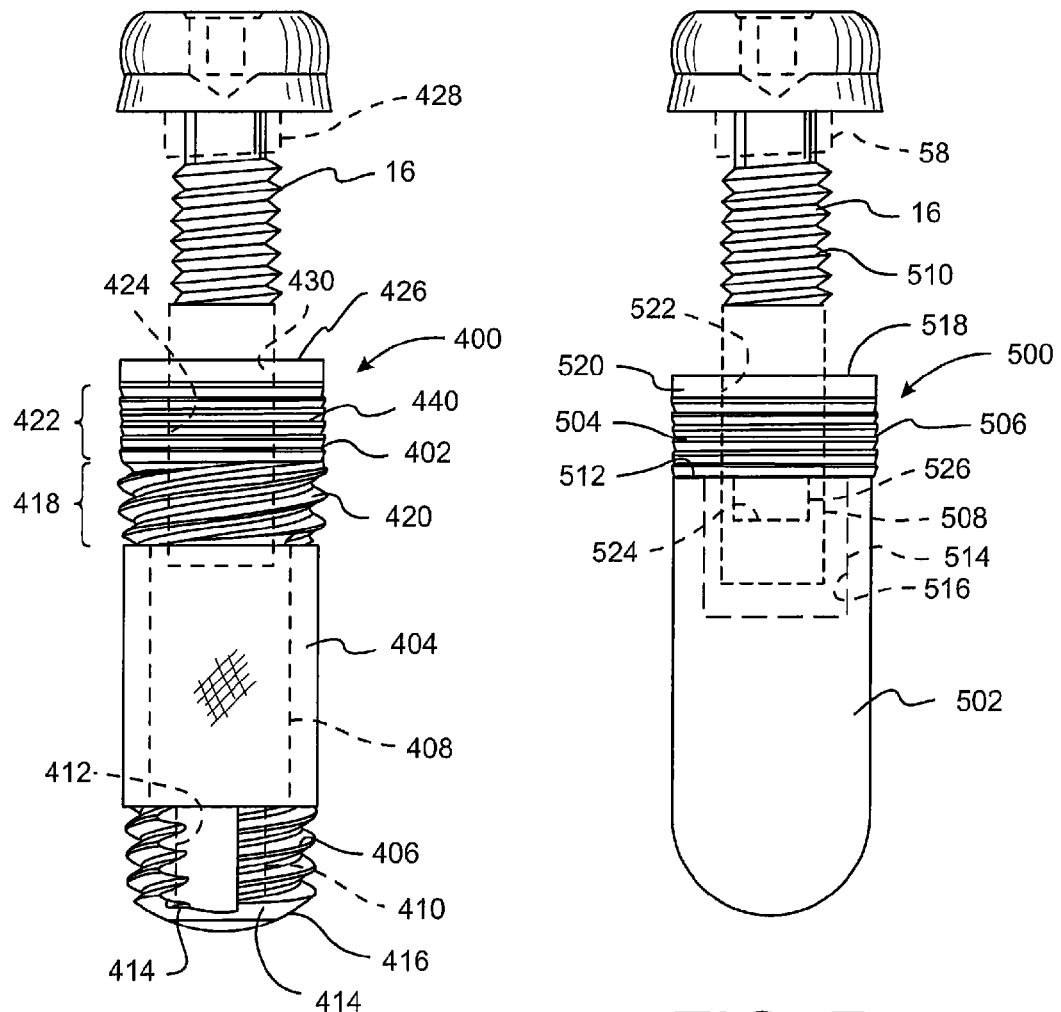
FIG. 6 is an exploded, side view of an alternative implant and a denture support piece.
FIG. 7 is an exploded, side view of a further alternative implant and a denture support piece.

Referring to FIG. 6, other alternative forms of the implant 12 are also contemplated. As shown, an implant 400 may support any of the denture support systems described herein. Implant 400 is a three piece implant with a coronal head portion 402, a porous metal portion 404, and an apical anchor or stem portion 406. A non-porous extension or core 408 extends apically from the coronal head portion 402, and has an apical end portion 410 that extends into a bore 412 on the anchor 406. The porous metal portion 404 is in the shape of a collar or sleeve, and in one form, has a radial thickness of about 0.03 inches (about 0.75 mm).

The porous metal portion 404 is mounted on the core 408 so that once the core 408 is secured to the anchor 406, the porous metal portion is secured to the implant 400 between the head portion 402 and the anchor 406 without the need to bond or weld the non-porous pieces to the porous metal portion. This avoids challenges that may be experienced when bonding a porous structure to a substrate due to the dissimilar materials, the reduced surface area of the porous material, and changes in both the porous metal material 40 and the coupling 16 caused by high temperature for example.

In the illustrated form, the anchor 406 may be laser welded to the apical end portion 410 of the core 408 thereby permanently securing the porous metal portion 404 on the core 408. Specifically, the apical end portion 410 and anchor 406 are welded together along a seam 414 at the apical end 416 of the anchor 406. It will be understood that many alternative configurations are contemplated (such as the head being integral to the anchor 406 or entirely separate instead of integral to the head portion 402) as long as the porous metal portion 404 is secured over the core 408 on the implant 400.

The exterior of the head portion 402 may be provided with a zone 418 of large threads 420 for insertion of the implant 400 into a bore in bone as well as for improved osseointegration and initial stability with cancellous bone. A more coronal zone 422 may have small threads, circumferential grooves 440, or other surface roughness structures or coating for the promotion of cortical bone growth. In one form, the grooves 440 are barb shaped so that the groove edges generally point coronally to bite into the surrounding bone and limit pull-out of the implant 400. If the head portion 402 has a zone extending into the gingiva, the surface of that zone may have a surface selected for promotion of soft tissue growth or barriers to limit soft tissue or bacteria from extending into the bone layers within the bore in bone.

As shown, implant 400 may also have an internal, axially extending bore 424 within the head portion 402 to receive any of the couplings described herein such as the coupling 16. In this case, however, the bore 424 extends within the non-porous material of the head portion 402. The head portion 402 may be made of the same materials as that mentioned above for anchor 64. Alternatively, the coupling may be welded to a coronal end 426 of the head portion 402 to effectively form a one-piece implant that supports a denture or bridge. In this case, the coupling 16 may have a short centering shaft 428 (shown in dashed line) to center the coupling on the implant 400. The shaft 428 is received in a short bore 430 (shown in dashed line) on the implant 400. The placement of the shaft 428 and the bore 430 on the coupling and implant may be reversed, and the bore and shaft may be connected to each other by friction fit, adherent, or other methods.

Referring to FIG. 7, in yet another alternative, an implant 500 has a porous metal portion 502 with a bullet shape and without a non-porous anchor part. In one form, the implant 500 may be made entirely of the porous material. In the illustrated form, however, a coronal non-porous portion 504 may be made of the same materials as that mentioned above for anchor 64. The coronal portion 504 may provide increased initial stability in the cortical bone and to support the coupling 16 (in this example). Thus, the coronal portion 504 may have small threads, circumferential grooves or barbs 506, or other surface treatment to engage the surrounding cortical bone.

The implant 500 has a number of different alternative configurations for securing the coronal portion 504 to the porous metal portion 502 and securing the coupling 16 to the coronal portion 504. In one form, the implant 500 has an internal bore 508 (shown in dashed line) that at least extends axially into the coronal portion 504, and in the illustrated form, also extends into the porous metal portion 502. In this alternative, the shaft 510 of the coupling 16 directly engages the porous metal portion 502 similar to that above described for bore 32 on implant 12. In this case, the coronal portion 504 is welded or otherwise bonded to a coronal surface 512 of the porous metal portion 504. In another alternative, the coronal portion 504 has an apically extending stem 514 (shown in dashed line) that extends into a large bore 516 extending axially into the porous metal portion 502. In this case, the stem 514 is secured in the larger bore 516 by friction fit, bonding, threading, and/or otherwise as mentioned above, and the coupling shaft 510 is secured within the head portion 504 and the non-porous stem 514 rather than the porous metal portion 502.

In yet another alternative form, the coupling 16 may be bonded to the coronal surface 518 of the coronal portion 504 while the coronal portion 504 is bonded to the coronal surface 512 of the porous metal portion 502 to form a permanently formed, one-piece implant. In this case, the coupling 16 may have the short shaft 58 (shown in dashed line) received by a short axial bore 522 (shown in dashed line) open on the coronal end 520 of the coronal portion 504. Similarly, the porous metal portion 502 may have a short axial bore 524 (shown in dashed line) that receives a short shaft 526 (shown in dashed line) extending from the coronal end portion 504. It will be understood that the male-female orientation of the shafts and short bores could be reversed.

Figure 8:
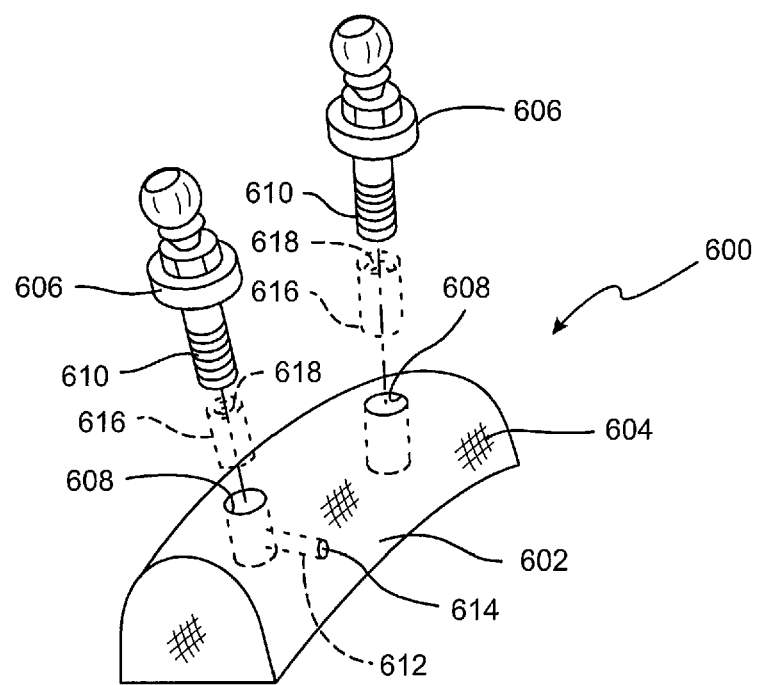
FIG. 8 is a perspective view of a block implant supporting multiple denture support posts.

Referring now to FIG. 8, an alternative is provided for alveolar ridges with significant defects such as low bone mass under multiple tooth locations. In this case, a single implant 600 may be used that is in the form of a block 602 of the porous metal material 604, and that supports one or more denture support system structures 606. In the illustrated form, the ball joint structure is shown from the denture support system 200 (FIG. 4).

In this form, the block 602 is shaped to fit the defect or the defect on the bone is shaped to receive the block. In either case, such a block may be shaped with CAD design techniques to provide a custom block that fits a particular patient's jaw if desired. Otherwise, the block may be provided in a standard size and subsequently shaped by the practitioner. The block 602 may have one or more bores 608 (here two are shown) to receive a coupling 610 like coupling 202 for example. The bores 608 may be threaded or otherwise provided for alternative connection to the couplings as described above. This includes one or more bores 612 (shown in dashed line) extending transverse to bores 608 and opening to bores 608 so that the coupling may be locked into bore 608 by a cross-pin or set screw 614. Also, the orientation and spacing of the bores 608 may also be custom designed for the particular patient and type of support system if needed.

In yet another approach, optional sleeves 616 may be provided for insertion into the bores 608 (or at least one bore) and that have internal threads 618 to engage the threads on the coupling 610. In one form, the sleeves 616 are made of titanium or other acceptable solid metal, and the sleeves 616 are fixed in the bores 608 by diffusion bonding, chemical vapor deposition (CVD) bonding, or other types of welding. Otherwise, the sleeves 616 may be fixed in the bores by friction or taper fit, the set screw 614, adhesives, and/or any other attachment device used herein. The sleeve 616 may even have external threads to act as an adapter.

It will be appreciated that any of the specific features of any of the single or multiple implant devices described herein may be used on any of the embodiments herein where it is consistent with that embodiment structure. Thus, for example, a sleeve and/or any of the attachment methods, such as bonding, used for the block 602 may also be used on any of the single implant embodiments of FIGS. 1-7 and vice versa.

It will be understood that while the block 606 is shown to only extend for a small arcuate section to support two couplings 610, the block 606 could extend mesially and distally to form a compete arch to hold an entire denture.

While this invention has been described as having a preferred design, the present invention can be further modified within the spirit and scope of this disclosure. This application is therefore intended to cover any variations, uses, or adaptations of the invention using its general principles such as for other than dental implants. Further, this application is intended to cover such departures from the present disclosure as come within known or customary practice in the art to which this invention pertains and which fall within the limits of the appended claims.

What is claimed is:

1. A dental implant device comprising:
   an implant portion for being placed in a bore and having a coronal end portion and a porous metal portion;
   a metal coupling having a coronal end configured as a male or a female connector, and an apical end integrally formed with the coronal end and configured to engage the porous metal portion;
   a metal connector element having an apical end configured as the other one of the male or the female connector for connection of the connector element to the metal coupling, and a coronal end configured as a second male or second female connector; and
   a resilient cap having a coronal end configured for connection to a denture support piece and an apical end configured as the other of the second male or the second female connector for connection to the metal connector element.

2. The device of claim 1, wherein the connection of the cap and the connector element comprises a snap-fit.

3. The device of claim 1, wherein the connection between the cap and the connector element comprises a ball joint that allows for articulation of the cap relative to the connector element.

4. The device of claim 1, wherein the device is configured to distribute occlusal forces received from the denture support piece.

5. The device of claim 1, wherein the implant portion forms a first bore at the apical end of the coupling and the coronal end portion comprises an extension received within the first bore.

6. The device of claim 5, wherein the extension of the apical end of the coupling is threaded into the first bore of the implant portion using class 1 thread specifications.

7. The device of claim 5, wherein the apical end of the metal coupling defines a second bore, and wherein the extension comprises a separately formed shaft received by the second bore for securing the implant portion to the coupling.

8. The device of claim 7, wherein the shaft has a coronal end threadably attached to the coupling and an apical end threadably attached to the implant portion.

9. The device of claim 8, wherein the coronal end of the shaft has a larger outer diameter than the apical end of the shaft and forms a shoulder therebetween.

10. The device of claim 9, wherein the shoulder is positioned on a coronal surface of the implant portion to limit advancement of shaft into the first bore.

\* \* \* \* \*